United States Patent [19]

Newbury

[11] Patent Number: 4,799,500

[45] Date of Patent: Jan. 24, 1989

[54] METHOD OF AND APPARATUS FOR TREATMENT OF MUSCLE IMBALANCE

[76] Inventor: Renton D. Newbury, 108 David Street, Dandenong, Victoria 3175, Australia

[21] Appl. No.: 913,444

[22] Filed: Sep. 30, 1986

[30] Foreign Application Priority Data

Sep. 17, 1986 [AU] Australia ............................... PH8081

[51] Int. Cl.⁴ ............................................... A61F 5/56
[52] U.S. Cl. ..................................... 128/859; 128/846
[58] Field of Search ................... 128/132 R, 136, 359; 433/6

[56] References Cited

U.S. PATENT DOCUMENTS

| | | | |
|---|---|---|---|
| 3,334,417 | 3/1965 | Spengeman | 32/14 |
| 3,488,848 | 1/1970 | Lerman | 433/25 |
| 3,924,638 | 12/1975 | Mann | 128/359 |
| 3,997,970 | 12/1976 | Hodgson | 433/19 |
| 4,211,008 | 7/1980 | Lerman | 433/229 |
| 4,433,956 | 2/1984 | Witzig | 433/7 |
| 4,519,386 | 5/1985 | Sullivan | 128/132 R X |
| 4,553,549 | 11/1985 | Pope | 128/421 |

FOREIGN PATENT DOCUMENTS

| | | | |
|---|---|---|---|
| 1147583 | 6/1983 | Canada | 433/6 |
| 1085421 | 2/1955 | France . | |

OTHER PUBLICATIONS

Newbury, Renton D. "Disturbance of Functional Occlusion Syndrome" *Australian Family Physician*, vol. 13, No. 1, Jan. 1984, pp. 31-35.

Gelb, Harold et al., "A Two-Year Clinical Evaluation of ZOD Cases of Chronic Headache" *JADA*, vol. 91, Dec. 1975, pp. 1230-1236.

Cavestani, Laura "Jaws: Doing the Old Bump and Grind" *Diet and Exercise*, 4/81. pp. 59-61.

Newbury Renton D., "The Myth of Migraine", *White Cross Journal*, Winter 1985, pp. 1-8.

*Primary Examiner*—Robert A. Hafer
*Assistant Examiner*—Kevin G. Rooney
*Attorney, Agent, or Firm*—Pollock, Vande Sande & Priddy

[57] ABSTRACT

The invention is based on the realization that the pain associated with many conditions such as headaches (in particular, migraines and other severe repetitive chronic headaches) is caused by a muscle imbalance that can be traced to the masticatory muscles controlling the lower jaw. It has been found that interdigitation of the molar teeth of the upper and lower jaws is the principal factor that causes the muscle imbalance. The treatment, therefore, requires the unlocking of the interdigitation. In this regard a particular construction of splint to overlie at least the molar teeth of the lower jaw is disclosed.

5 Claims, 1 Drawing Sheet

METHOD OF AND APPARATUS FOR TREATMENT OF MUSCLE IMBALANCE

FIELD OF THE INVENTION

The present invention relates to the treatment of muscle imbalance.

BACKGROUND AND SUMMARY OF THE INVENTION

It is well known that substantial pain and resultant inconvenience is associated with a range of conditions, such as headaches (in particular, migraine and severe repetitive chronic headaches), temperomandibular joint pain dysfunction, whiplash and other neck complaints, repetitive strain injury and other arm, wrist and hand muscle complaints, chronic back pain, various eye complaints (e.g. diplopia, astigmatism, photophobia, lazy eye), dyslexia and various ear complaints, from which all members of the community suffer to varying degrees. Whilst there is a wide range of treatments for the relief of the pain associated with the conditions such treatments are of variable effectiveness and in many situations do not relieve entirely the pain or prevent the recurrence of the conditions.

The object of the present invention is to alleviate the pain caused by the above conditions and to minimize the likelihood of recurrence of the conditions.

According to the present invention there is provided a method of treating muscle imbalance comprising, unlocking the interdigitation of the teeth of the upper and lower jaws to allow the muscles supporting the jaws to function correctly and thereby to move the lower jaw in a preferred path during mastication, as described herein.

The term "preferred path during mastication" as used herein is understood to mean generally horizontal circular movement of the lower jaw with respect to the upper jaw without interference of the teeth.

It is preferred that the interdigitation of the teeth is unlocked by positioning a splint over at least the molar teeth of the lower jaw, the splint having a contact surface for at least the molar teeth of the upper jaw which prevents direct contact between the molar teeth of the upper and lower jaws and repositions the molar teeth of the lower jaw with respect to the upper jaw to permit movement of the lower jaw in the preferred path.

In a preferred arrangement the method comprises adjusting the contact surface periodically to increase the spacing between the molar teeth in the upper and lower jaws thereby to allow the muscles supporting the lower jaw to relax and function at their correct length and tone.

According to the present invention there is also provided a splint for the lower jaw of a patient, said splint comprising a contact surface for at least the molar teeth of the upper jaw for preventing interlocking interdigitation of the molar teeth thereby to allow the muscles supporting the jaws to move the lower jaw in a preferred path, as described herein.

In a preferred arrangement the thickness of the splint is selected to separate the molar teeth of the upper and lower jaws by a sufficient distance to allow the muscles supporting the jaws to function optimally, thereby relieving any build up of stress in the muscles.

It is preferred that the contact surface is formed so that there is point contact between each molar tooth of the upper jaw and the contact surface. It is particularly preferred that the point contact is between the lingual cusps of each molar tooth of the upper jaw and the contact surface.

It is preferred that the contact surface is formed so that when the molar teeth of the upper jaw contact the splint, the molar teeth are inclined outwardly and downwardly in the range of 15° to 25° measured with respect to a vertical axis. It is particularly preferred that the angle of inclination is 20°.

It is preferred that the splint comprises two arms and a bridge interconnecting the arms, and that the arms are formed to overlie the molar teeth on respective sides of the lower jaw. In a particularly preferred arrangement the arms extend rearwardly from the second premolars and do not overlie the first premolars and the incisors. Preferably each arm is generally U-shaped in transverse section with a dome shaped central section separating two sides.

According to the present invention there is also provided a method of treating muscle imbalance comprising:

(a) modifying the orientation of the jaws of a patient with respect to each other, and (b) adjusting the separation of molar teeth of the lower jaw and the upper jaw when the jaws are in a closed position.

The present invention is based on the realization that the pain associated with many conditions is caused by a muscle imbalance that can be traced to the masticatory muscles controlling the lower jaw. The conditions include headaches (in particular migraine and severe repetitive chronic headaches), temperomandibular joint pain dysfunction, whiplash and other neck complaints, repetitive strain injury and other arm, wrist and hand muscle complaints, chronic back pain, various eye complaints (e.g. diplopia, astigmatism, photophobia, lazy eye) and various ear complaints.

The muscle imbalance is caused by a number of factors. However, it is believed that the principal factor is a particular type of interdigitation of the molar teeth which interferes with the normal masticatory movement of the teeth, i.e. generally circular horizontal movement of the lower jaw with the molar teeth of the upper and lower jaws in contact. In extreme cases the interdigitation restricts the movement of the mandible to movement up and down vertically during mastication which in turn causes abnormal functioning of the masticatory muscles. One consequence of the abnormal functioning is that the balance of the muscles is disturbed and this leads to muscle spasm, pain and dysfunction, all of which can be traced by the patient to the general region in the body in which the muscles are located.

Furthermore, the imbalance in the masticatory muscles is transferred to muscles which are connected directly to or are associated with the masticatory muscles. Similarly, the imbalance in these muscles leads to muscle spasm, pain and dysfunction, all of which are experienced by the patient in the region of the body in which the muscles are located. For example, an imbalance in the Masseter muscle, one of the masticatory muscles, may lead to the patient experiencing pain in the facial region. The muscular connections and associations are sufficiently extensive that any imbalance in the masticatory muscles may be transferred extensively throughout the body to regions such as the neck, shoulder, lower back, arms and legs.

In many situations, the imbalance in the masticatory muscles and muscles connected directly to or associated with the masticatory muscles is such that the pain is at a tolerable level and is not regarded by the patient as being of an abnormal nature requiring treatment. In such situations an external event such as a motor car accident or an overworking of imbalanced muscles may aggravate the imbalance to the extent that the pain exceeds the tolerable level.

For example, in the case of motor car accidents in which a person experiences whiplash, the hyperflexion of the muscles in the neck region increases the imbalance of the muscles in the region to the extent that the patient experiences considerable pain. The treatment of the pain as a symptom of whiplash may alleviate the pain to a certain extent, but in many instances does not correct the imbalance in the muscles to the previous tolerable level, in which case the patient continues to report pain. As a consequence, the whiplash injury is considered to be far more serious than would be expected in view of the particular circumstances of the motor car accident. In other words, the motor car accident tends to direct the clinician away from the actual cause of the pain, namely the pre-existing imbalance in the muscles.

Another example relates to overworking of muscles in the arm due to carrying out repetitive manual functions. If the muscles in the arm are unbalanced, due to the transference of an imbalance in the masticatory muscles, the repetitive working of the muscles in the arm may aggravate the imbalance to the extent that pain above a previously tolerable level is experienced by the patient. Given the absence of a history of pain in the muscles of the arm the logical conclusion is that the injury is due to the repetitive manual functions and the injury is classified as a repetitive strain injury with treatment selected accordingly. Such a diagnosis overlooks the fact that if the muscles were not unbalanced then the muscles might have been able to cope with the manual work considered to be the cause of the repetitive strain injury.

In both examples noted above, the treatment of the cause of the initial imbalance, i.e. treatment of the imbalance in the masticatory muscles, has the effect of allowing the other muscles to which the imbalance is transferred to work in the normal manner with the result that the external influence such as the motor car accident or the excessive working of the muscles in the arm does not result in the extreme symptoms that characterize many injuries considered to be attributable to the external influences.

BRIEF DESCRIPTION OF THE FIGURES OF THE DRAWINGS

A further detailed description of the present invention is now provided with reference to the accompanying drawings, in which.

DETAILED DESCRIPTION OF THE PREFERRED EMBODIMENT

Figure 1:
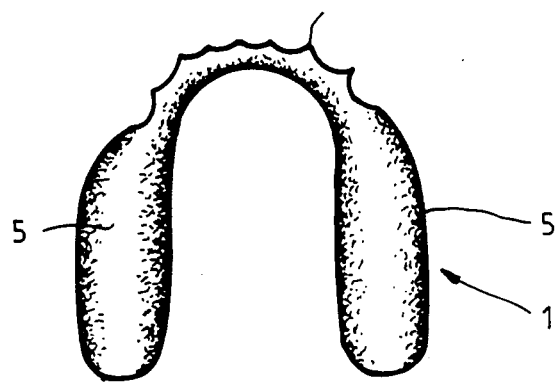
FIG. 1 is a plan view of a splint for use in the treatment of muscle imbalance.
Figure 2:
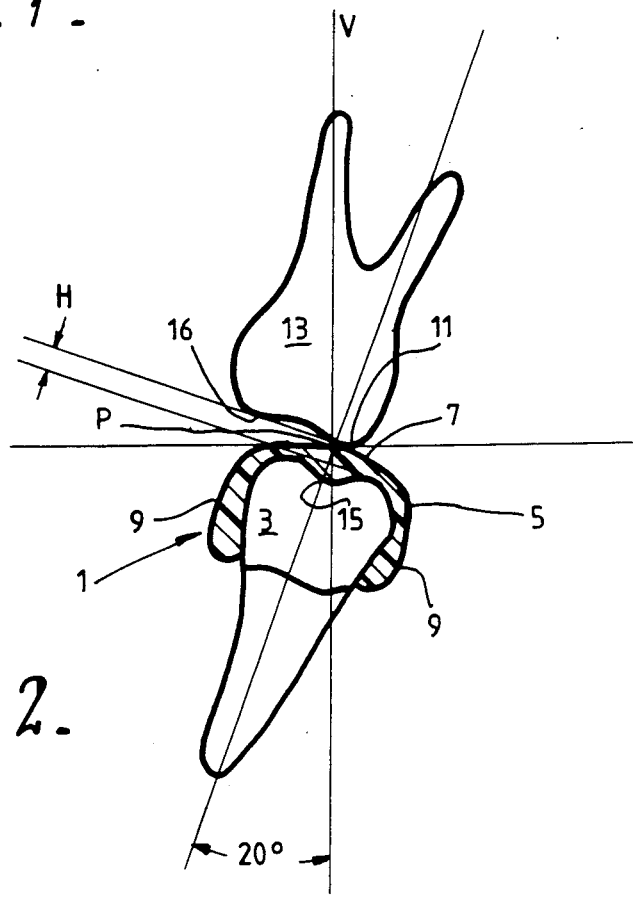
FIG. 2 is a section illustrating the preferred contact between the molar teeth of the upper jaw and the splint shown in FIG. 1.

The splint 1 shown in FIGS. 1 and 2 is moulded from plastics material to fit snuggly over the teeth of the lower jaw of a patient. The splint 1 comprises two arms 5 and a central bridge section 6. As is described in more detail below, each arm 5 is formed to overlie at least the molar teeth on one side of the lower jaw. It is preferred that the splint is formed so that the arms extend rearwardly from the second premolars and do not overlie the first premolars and the incisors. The central bridge is formed to extend behind the incisors and canine teeth of the lower jaw to minimize the extent to which the splint detracts from the external appearance of the teeth.

As can best be seen in FIG. 2, each arm 5 of the splint 1 is generally U-shaped in transverse section and comprises a dome shaped contact surface 7 and two sides 9.

The section shown in FIG. 2 is through the molar teeth on the left hand side of the jaw viewed posteriorly (i.e. from the rear towards the front). The section illustrates the correct relative location of the teeth of the upper and lower jaws, which is characterized by the teeth 3 of the lower jaws being positioned slightly inside the teeth 13 of the upper jaw so that the lingual cusps 11 of the teeth 13 of the upper jaw are above the hollow 15 in the teeth 3 in the lower jaw.

The dome shaped contact surface 7 of the splint 1 is formed so that there is substantially point contact P with the lingual cusp 11 of the teeth of the upper jaw.

Another important, although by no means essential, requirement is that the dome shaped contact surface 7 is formed or the teeth 13 of the upper jaw are ground so that there is substantially no contact between the buccal cusps 16 of the teeth 13 of the upper jaw and the splint 1.

It should be noted that the use of the splint 1 is not restricted to dentate patients and is equally applicable for use with edentulous patients. Furthermore, the use of the splint 1 on dentate patients is not dependent on all of the molar teeth of the patient being present and can be adapted for use with patients who are missing some or all of the molar teeth.

It should be noted that it has been found that it is preferably to form the dome-shaped contact surface 7 so that when the teeth of the upper and lower jaws are in contact the molar teeth of the upper jaw are inclined outwardly and downwardly at an angle in the range of 15° to 25° measured with respect to a vertical line V. As can be seen from FIG. 2 it is particularly preferred that the angle of inclination is 20°. The significance of the inclination of the molar teeth of the upper jaw to the molar teeth of the lower jaw is that it means the teeth are self seating under chewing pressure and that the lower jaw moves in the preferred path during mastication. It should be noted that the teeth of the upper jaw closer to the front of the mouth have less outward inclination, viz. the second premolar has a 10° outward inclination, the first premolar and cuspid have a 10° inward inclination which makes them generally unstable for correct chewing movement.

Further, it has been found that attention to the preferred inclination of the molar teeth of the upper jaw during adjustment of the splint 1 or during cutting the buccal cusps 16 of the molar teeth of the upper jaw is a useful means to ensure positive splint action. The foregoing comments are particularly relevant to edentulous patients where there are more variables working against successful treatment.

The splint 1 described above is used in a preferred method of treating muscle imbalance in accordance with the present invention as a means to unlock malocclusive interdigitation of the teeth. As indicated previously, such interdigitation prevents normal masticatory movement of the teeth of the lower jaw with respect to the teeth of the upper jaw. The interruption of normal masticatory movement of the teeth unbalances the masticatory muscles and muscles connected directly to or associated with the masticatory muscles, and the muscle imbalance is reflected in pain experienced by the patient in the region of the muscles. (For a detailed description of the masticatory muscles reference is made to Gray's Anatomy [36th edition] published by Churchill Livingstone).

As can readily be appreciated from the drawings the splint 1 unlocks interdigitation by separating the teeth of the upper and lower jaws so that the malocclusions in the teeth do not interrupt masticatory movement of the jaws. However an arbitrary vertical separation of the teeth is not in itself sufficient for successful treatment and it has been found that it is preferable that the splint is formed to produce:

1. an anterior open bite between the incisors with the posterior teeth closed on the splint 1,
2. symmetrical bilateral even contact of the molars and the second premolars of the upper jaw with the splint 1, and
3. unimpeded correct circular grinding movements with no inclined slides.

In order to achieve an interior open bite it is important initially to adjust the splint height (H in FIG. 2) so that, when the patient performs circular grinding movements with the posterior teeth in contact with the splint 1, there is substantially no contact or interference between the anterior teeth (i.e. the incisors to first premolars) of the upper and lower jaws. The splint height conveniently is set to allow for a separation of approximately 1 mm or less between the incisors in the upper and lower jaws. As will be described hereinafter the height is increased during a subsequent stage in the treatment.

In order to produce symmetrical bilateral even contact of the molars and second premolars of the upper and lower jaws the pressure of contact is reduced from medium to heavy contact between the 2rd molars (or the 3rd molars if present and useful) to relatively light contact between the second premolars. It should be noted that it is important that there are sufficient usable molar teeth in the upper jaw to produce symmetrical even contact. It is believed that the minimum number of teeth necessary in this regard is two molars and the second premolar on each side of the upper jaw. It has been found that the use of the splint with patients having only a first molar in the upper jaw may bring relief but not a cure. Thus, in situations where the patient is partially dentate it may be necessary to fit a partial denture in the upper jaw.

The unimpeded circular grinding movements with no inclined slides are achieved by grinding the contact surfaces of the splint so that:

(a) there is substantially equal contact pressure on corresponding sections of the left and right sides,
(b) as previously indicated the splint 1 is dome shaped downwardly towards the buccal and lingual sides to ensure point contact of the lingual cusps 13 of the teeth of the upper jaw and the splint 1, and
(c) the contact surfaces are reasonably smooth.

As is indicated above, after the initial fitting of the splint 1 to a patient the height H of the splint is adjusted progressively to return the masticatory muscles to the correct working length, bearing in mind that it has been found that if the height H is too high there will be an increase in the severity of the symptoms. Basically, the adjustment of the height of the splint 1 is a matter of trial and error.

It is preferred that the splint 1 is worn continuously in order to ensure correct contact between the teeth of the upper and lower jaws. As can readily be appreciated such correct contact is desirable during eating. However, there are other instances in the course of the day during which there is significant contact of the teeth. For example, during saliva swallowing the teeth tap together to locate the upper and lower jaws whilst the muscles perform the swallowing action. Typically, a person swallows approximately 2000 times per day. In addition, during sleep the sub-conscious attempts to restore normal function of the masticatory muscles by initiating grinding of the teeth to eliminate the dental malocclusion. After a period of time, such grinding becomes habitual and is commonly known as bruxing. It can be appreciated from the above that continuous use of the splint 1 is desirable to ensure consistent correct operation of jaws during the course of the day.

It has been found from an experimental test program with a selection of patients that the following treatment periods with the splint 1 to substantially eliminate the pain resulting from the muscle imbalance are typical:

(a) Teenage to mid-twenties: 2 to 3 months.
(b) Late twenties to late thirties: 6 to 10 months.
(c) Over 40: 6 to 12 months or more, although generally difficult to predict.

It should be noted that the above results relate principally to the treatment of patients having migraines and other severe repetitive chronic headaches.

The above treatment times can be understood in the context that the method of treatment of the present invention is concerned with returning the masticatory muscles to a normal function and tone, and the older the patient and the longer the condition has been present the more difficult it is for the masticatory muscle to recover.

In some situations, after successful treatment it is possible to correct the malocclusions in the teeth of the patients which resulted in the initial interdigitation and muscle imbalance by selective grinding of the teeth and other dental procedures, thereby to allow the masticatory muscles to move the lower jaws in the correct circular path unaided by the splint 1. However, such procedures are restricted to patients having a fairly normal set of teeth with minimal malocclusions that require correction with a splint 1 having a relatively low optimum height H.

With most patients it is not possible to dispense with a form of splint 1 and usually, once the treatment has been completed, the plastic splint 1 is replaced with a more durable splint (not shown) formed from a cobalt chrome alloy.

Many modifications may be made without departing from the spirit and scope of the present invention.

I claim:

1. A splint for the lower jaw of a patient to prevent interlocking interdigitation of the molar teeth thereby allowing the muscles supporting the jaws to move the lower jaw in a preferred path, said splint comprising two arms and a bridge interconnecting the arms, each arm being generally U-shaped in transverse section with a dome-shaped central section separating two sides, the dome-shaped central section defining a contact surface for at least some of the molar teeth and the second premolar teeth and not for the first premolar teeth, the incisor teeth and the canine teeth of the upper jaw, the dome-shaped central section having a thickness to provide a selected spacing between the molar teeth of the upper and lower jaws, and the dome-shaped central section being formed so that there is point contact between each molar tooth of the upper jaw and the contact surface.

2. The splint as claimed in claim 1, wherein the thickness of the dome-shaped central section is selected to separate the molar teeth of the upper and lower jaws by a sufficient distance to allow the muscles supporting the jaws to function optimally, thereby relieving any build up of stress in the muscles.

3. The splint as claimed in claim 1, wherein the point contact is between the lingual cusps of each molar tooth of the upper jaw and the contact surface.

4. The splint as claimed in claim 1, wherein the contact surface is formed so that when the molar teeth of the upper jaw contact the splint, the molar teeth are inclined outwardly and downwardly in the range of 15° to 25° measured with respect to a vertical axis.

5. The splint as claimed in claim 4, wherein the angle of inclination is 20°.

* * * * *